United States Patent [19]

Thiele et al.

[11] 4,211,551

[45] Jul. 8, 1980

[54] HERBICIDE

[75] Inventors: Kurt Thiele; Quazi Ahmed, both of Zofingen; Walter Schären, Vordemwald; Jacques Meyer, Zofingen, all of Switzerland

[73] Assignee: Siegfried AG, Zofingen, Switzerland

[21] Appl. No.: 850,468

[22] Filed: Nov. 10, 1977

[30] Foreign Application Priority Data

Nov. 15, 1976 [CH] Switzerland ..................... 014340/76

[51] Int. Cl.² ............................................. A01N 9/24
[52] U.S. Cl. ......................................... 71/116; 71/88; 71/94; 260/501.16; 544/107; 562/468; 546/192
[58] Field of Search .......................................... 71/116

[56] References Cited

U.S. PATENT DOCUMENTS 4,088,474  5/1978  Matterstock et al. ............. 71/116 X Primary Examiner—Catherine L. Mills
Attorney, Agent, or Firm—Werner W. Kleeman

[57] ABSTRACT

Herbicidal compositions for selective weed control comprising 4-(4'-chlorobenzyl)-phenoxy acetic acid or a salt thereof and the novel salts of 4-(4'-chlorobenzyl)-phenoxy acetic acid.

A method for selectively controlling weeds by applying to a crop area an effective amount of 4-(4'-chlorobenzyl)-phenoxy acetic acid or a salt of said acid.

1 Claim, No Drawings

HERBICIDE

BACKGROUND OF THE INVENTION

1. Field of the Invention

The present invention relates to herbicides and more particularly to compositions and methods for selectively controlling weeds.

2. Description of the Prior Art

Weed control for agricultural purposes remains a topic of great importance even though many different classes of compounds as well as thousands of specific compounds have been disclosed in the literature for the purposes of both general and selective weed control. A high degree of herbicidal or weed controlling effectiveness is an important aim in weed control, and the problem of controlling weeds in agricultural and horticultural crop areas where both weeds and crop plants belong to similar families has not been solved satisfactorily. Possibly, no generally applicable approach to selectively controlling specific plants or weeds within a given crop is feasible and research aiming at new compounds and methods for selective weed control is being continued all over the world. Further, environmental problems such as residual components of agrochemical agents represent a problem of increasing importance and it is essential to find and use such weed control agents that are not harmful to animals and humans nor produce residual compounds that have such undesired effects.

German Published Patent Application No. 2,417,487 discloses that a class of compounds, i.e. the benzyl phenoxy alkanoic acids as well as derivatives thereof, is suitable for selective weed control purposes and such compounds show a remarkable degree of selective herbicidal or weed control effectiveness against undesired growth of the Graminae or grass-type(monocotyledonous) plants while being substantially inactive against dicotyledonous species.

A structurally related group of chemical compounds has been disclosed by us previously for therapeutic lipid lowering purposes, i.e. for reducing the colesterol or fat content of the blood, c.f. for example our German Published Patent Application No. 2,461,069. In accordance with the present invention we have found that a specific compound previously disclosed by us as a lipid lowering agent and its salts not previously disclosed have a surprisingly high degree of herbicidal effectiveness against both weeds of the monocotyledonous and dicotyledonous species. Specifically, it has been discovered that the 4-(4'-chlorobenzyl)-phenoxy acetic acid as well as the salts of said acid provide for the improved herbicidal effects just mentioned when used for selective weed control in pre-emergence and/or post-emergence type applications.

SUMMARY OF THE INVENTION

Thus, according to a first embodiment, the invention provides for a novel herbicidal composition comprising, as an active ingredient, 4-(4'-chlorobenzyl)-phenoxy acetic acid or a salt thereof.

According to a second embodiment, the present invention provides for a method of selectively controlling weeds that infest crop areas by applying to such area a herbicidally effective amount of 4-(4'-chlorobenzyl)-phenoxy acetic acid or a salt thereof.

According to a third embodiment, the invention provides for novel salts of 4-(4'-chlorobenzyl)-phenoxy acetic acid.

DETAILED DESCRIPTION OF THE INVENTION 4-(4'-chlorobenzyl)-phenoxy acetic acid (hereinafter referred to as CBPA) has the structural formula

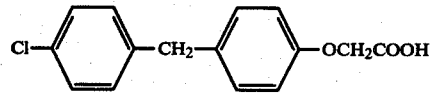

and methods suitable for the preparation of CBPA have been disclosed in our above mentioned German Patent Application No. 2,461,069. Other methods will be disclosed below. CBPA is known to have a low acute oral toxicity, i.e. an $LD_{50}$ of 2700 mg per kilogram of body weight (determined on mice). Such low toxicity of CBPA and its salts with cations known to be non-toxic is of advantage in weed control.

CBPA can be prepared, for example, by hydrolysis of one of its functional derivatives, i.e. a precursor of CBPA, for example the 4-(4'-chlorobenzyl)-phenoxy acetonitrile. Another method is based upon the reaction of 4-(4'-chlorobenzyl)-phenol with formaldehyde in the presence of a polyhalogenated methane derivative, for example chloroform, and a strong base such as sodium hydroxide. A simple method of synthesizing CBPA is condensation of 4-(4'-chlorobenzyl)-phenol with haloacetic acid, e.g. chloroacetic acid. A specific example of this method will be given below.

While CBPA itself is a surprisingly effective herbicidal agent for selective weed control, the salts of this acid with organic or inorganic bases are suitable for this purpose as well and constitute a preferred group of herbicides according to the invention. Said salts have the structural formula (I)

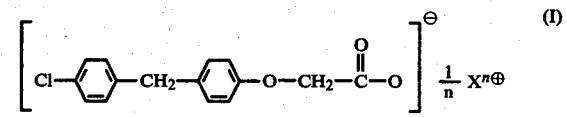

wherein X is a cation selected from alkali metal cations, preferably sodium and potassium, alkaline earth metal cations, preferably calcium, ammonium and aminium cations; and n is the valency of said cation.

Preferred aminium cations have the formula

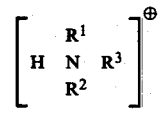

wherein $R^1$, $R^2$ and $R^3$ are the same or different and are selected from the group consisting of hydrogen, $C_1$-$C_{10}$ straight or branched chain alkyl, $C_1$-$C_{10}$ hydroxy substituted straight or branched chain alkyl, $C_4$-$C_8$ cycloalkyl, $C_6$-$C_{12}$ aryl and $C_6$-$C_{12}$ aralkyl, e.g. benzyl, and wherein any two of $R^1$, $R^2$ and $R^3$ may be joined to form a 5 to 6 membered heterocyclic ring with the nitrogen atom, e.g. the piperidino or morpholino group; with the proviso that at least one of $R^1$, $R^2$ and $R^3$ is not hydrogen. When all $R^1$, $R^2$ and $R^3$ are hydrogen, the cation is the ammonium cation mentioned above as another preferred cation.

Salts of formula (I) can be obtained by conventional salt preparing methods, i.e. by reacting the acid CBPA with a base. Depending upon the type of base (ionic or proto-ionic) used, synthesis of the salt will include the formation of water when the base is ionic, e.g. NH$_4$OH, or will be an addition reaction when using a proto-ionic base, e.g. NH$_3$, instead of NH$_4$OH. A group of preferred bases suitable for forming the inventive salts have a basic dissociation constant greater than $1 \times 10^{-7}$, e.g. in the range of from $1 \times 10^0$ to $1 \times 10^{-6}$.

Generally, when forming salts of CBPA with alkali or earth alkali metals, the corresponding base, e.g. hydroxide, oxide or carbonate of sodium, potassium, calcium or ammonium, can be reached with CBPA. When forming the salt of CBPA by addition, a suitable amine base has the structure

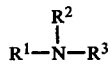

wherein $R^1$, $R^2$ and $R^3$ are as defined above. Specific examples of such amines include dimethyl amine, diethyl amine, benzyl amine, morpholine, piperidine, ethanol amine, diethanol amine and triethanol amine. Generally, the salts are prepared by reacting CBPA, if desired in the presence of a suitable solvent, at ambient temperature (10° to 30+ C.) with an equivalent amount of an organic or inorganic base of the type set forth above. The following examples illustrate the method of preparation. Percentages are by weight unless mentioned otherwise.

EXAMPLE 1

Preparation of 4-(4'-chlorobenzyl)-phenoxy acetic acid ("CBPA")

A mixture of 136.0 g of 4'-chloro-4-hydroxy diphenyl methane, i.e. p-(p'-chlorobenzyl)-phenol, 59.0 g chloroacetic acid and 57.6 g of sodium hydroxide in 600 ml of water was agitated for a period of 6 hours under nitrogen and at reflux temperature. A clear solution was obtained which forms a crystalline precipitate if left to stand at room temperature. The clear solution was acidified with 5 n hydrochloric acid and subsequently extracted with dimethyl ether to exhaustion. The combined extracts were evaporated to dryness under reduced pressure. The residue was treated with a 10% aqueous sodium bicarbonate, filtrated and washed several times with dimethyl ether to remove the non-reacted phenolic starting substance. The product was again acidified with 5 n hydrochloric acid and extracted with dimethyl ether. The solution in dimethyl ether was washed with water, dried over anhydrous magnesium sulfate and evaporated under reduced pressure. The residue was crystallized from acetone, and the target CBPA was obtained in an amount of 87.2 g in the form of white crystals having a melting point of 131°-133° C. The yield, calculated on the basis of the recovered phenolic starting substance, was 86%.

Analysis calculated for $C_{15}H_{13}ClO_3$: C 65.10%, H 4.73%, Cl 12.81%. found: C 65.00%, H 4.66%, Cl 13.11%.

EXAMPLES 2-5

CBPA prepared according to Example 1 was used for preparation of the following salts by reacting CBPA at ambient temperature with a substantially equimolar amount of benzyl amine, diethyl amine, morpholine and piperidine, respectively. The melting points (mp) of the salts obtained are as follows:

| | |
|---|---|
| CBPA benzyl amine salt | mp 156–157° C. |
| CBPA diethyl amine salt | mp 110–114° C. |
| CBPA morpholine salt | mp 126–128° C. |
| CBPA piperidine salt | mp 100–101° C. |

APPLICATION

The herbicidal compounds of this invention, i.e. CBPA and its salts with anorganic or organic bases are capable of selectively controlling weeds, notably in a crop area. Representative examples of weeds that can be selectively controlled in crop areas by application of the compounds of this invention are Shepherds Purse (Capsella bursa-pastoris), Lambs Quarters (Chenopodium) album), Rough Henbit (Lamium purpureum), Camomile (Matricaria chamomilla) and Chickweed (Stellaria media) by pre-emergence or post-emergence treatment in crops, such as green beans, Indian corn and barley. A particularly beneficial and high degree of effectiveness of CBPA and its salts has been found when controlling weeds of the Graminae family, such as Barnyard grass (Echinochloa crus-galli), Annual meadow-grass (Poa annua) and Wild Oat (Avena fatua). Because of the high herbicidal activity of CBPA and its salts, herbicidal control can be achieved at relatively low rates, e.g. in the range of from about 1.5 pounds of the active ingredient per acre to about 8 pounds per acre (equivalent to a range of from about 2 kilograms per hectare to about 10 kilograms per hectare).

It is of notable interest that the herbicides disclosed in the German Patent Application No. 2,417,487, i.e. the prior art benzyl phenoxy carboxylic acid herbicides, while having good herbicidal effects against undesired weeds of the Graminae family, are substantially inactive against dicotyledonous plants. In contrast, CBPA and the salts thereof show a remarkable degree of effectiveness both against monocotyledonous as well as dicotyledonous weeds both in pre-emergence and in post-emergence treatment.

COMPOSITIONS

Herbicidal compositions according to the invention comprise at least one active ingredient, i.e. CBPA or/and one or more salt(s) thereof, in combination with at least one second constituent which is a diluent and/or surfactant. The diluent(s) and surfactant(s) can be a solid or a liquid.

Depending upon the type of application, the inventive composition will include from about 1 to about 99% of CBPA and/or CBPA salt. The composition can be a slurry, a solution, a dust, an emulsion, a concentrate, a granulate, a wettable powder or the like.

Such compositions of this invention can be prepared in conventional ways. Sprayable compositions can be used without dilution or can be extended in suitable media. High strength compositions or concentrates will generally be used as intermediates for further formulation. Typically, such compositions will contain these ingredients in the following approximate proportions:

|  | Active ingredient | Diluent(s) (% by weight) | Surfactant(s) |
|---|---|---|---|
| Wettable powders | 20–90 | 10–80 | 1–10 |
| Solutions and suspensions | 5–50 | 50–95 | 0–15 |
| Aqueous solutions and suspensions | 10–50 | 40–84 |  |
| Dust compositions | 1–25 | 70–99 | 0–5 |
| Concentrates | 90–99 | 0–10 | 0–2 |

Lower or higher levels of active ingredient can be present depending upon the intended use. Higher ratios of surfactant to active ingredient may be desirable and can be achieved by incorporation into the formulation or by tank mixing.

The active CBPA or salt thereof may also be formulated or mixed in an applicator tank. Inventive compositions may further include agents for the control of pests, modification of growth, nutrition or for the control of plant diseases.

A suitable solid diluent is any particulate inorganic and organic substance of the type used in the herbicide or pesticide art. Representative examples include diatomaceous earth, fine silica, clay, kaolin, feldspar, talc, glass, quartz, wood flour, synthetic fertilizers, dried and pulverized biological sludge and the like. Many suitable solid diluents from the herbicide or insecticide art can be used, e.g. as described by Watkins et al in "Handbook of Insecticide Dust Diluents and Carriers", Caldwell, NJ. Typical liquid diluents and solvents are described in Marsden, "Solvents Guide", 2nd Edition, Interscience, New York, 1950. A solubility of less than 0.1% is preferred for suspension concentrates; solution concentrates should be substantially stable against phase separation at 0° C.

Suitable surfactants are those conventional in the herbicide art, e.g. as listed in "McCutcheon's Detergents and Emulsifiers Annual", MC Publ. Corp., Ridgewood, NJ, as well as in the "Encyclopedia of Surface Active Agents" by Sisely and Wood, Chemical Publ. Co., Inc., New York, 1964. Representative examples are sulfonated hydrocarbons, polyalkylene ether alcohols, "Carbowaxes", "Tween", etc.

In general, the term "surfactant" as used herein includes dispersing agents, wetting agents and the like.

All compositions can also contain conventional additives, e.g. to reduce foam, caking, corrosion or microbiological growth, or adhesives, binding agents and other types of adjuvants and compounding additives.

Methods of making such compositions are well known per se. For example, a solution can be prepared by simply mixing the active ingredient and a solvent. Fine solid compositions can be made by blending and, usually, grinding, e.g. in a hammer or fluid mill. Suspensions can be prepared by wet milling.

The method and composition aspect of the invention are further illustrated by the following examples.

EXAMPLE 6

A spray powder composition was prepared with the following ingredients:
50% of 4-(4'-chlorobenzyl)-phenoxy acetic acid (CBPA)
2.5% of a first surfactant or wetting agent (commercial alkyl aryl sulfonate)
5% of a second surfactant or dispersing agent (commercial sodium salt of a phenol sulfonic acid condensate)
12.5% of silica (filler-type)
30% of kaoline (filler-type)

The constituents were blended, coarsely milled and passed through a fluid mill to produce particles of active ingredients that are all below about 20 microns in diameter. The product was reblended before packaging. For use of this composition in selective weed control, the composition was suspended in a desired amount of water and applied to the area that was to be treated, typically in an amount of about 5 to about 15 kilograms of the composition per hectare of the area.

EXAMPLE 7

The composition prepared according to example 6 was used in field tests and compared with a composition of the type set forth in example 6 with the modification that the CBPA was replaced by the same amount of a conventional herbicide, i.e. Methabenzthiazuron (BSI approved common name). A "logarithmic" spraying apparatus of the type known in herbicide evaluation was used for these tests. This apparatus comprises an elongated spraying device connected with a reservoir for the composition to be tested, and a water reservoir. Separate test areas were sprayed with this apparatus and each composition was applied as an aqueous suspension. When operating the apparatus, water from the reservoir will gradually dilute the concentration of the composition and if the apparatus is taken at a constant speed over the strip of area to be treated, the concentration of the spraying liquor and, thus, the concentration of the active ingredient applied to the test area will be gradually reduced over a distance. The apparatus was operated such that the initial concentration of the active ingredient was equivalent to 10 kg/ha and decreased as follows:

| Distance from start (in meters): | 0 | 3 | 6 | 9 | 12 |
|---|---|---|---|---|---|
| Amount of active ingredient per hectare | 10 | 6.7 | 4.3 | 2.65 | 1.65 |

The amount of water applied by the apparatus remained constant and was equivalent to 666 liters per hectare. The tests were made in early August of 1976. The test areas were seeded with crop plant on a substantially weed-free soil, a middle-heavy sandy clay. One test area (zero-control) was seeded but not sprayed. Four weeks thereafter, the treated areas were inspected to determine the number of individual weed plants per square meter for five significant types of weeds and to calculate the percent effect according to the formula $$AK - AB/AK \cdot 100$$

wherein AK is the number of the individual plants of the specific weed in the untreated zero-control area and AB is the corresponding number of weed plants in the treated area. The results of these tests for three different dosage amounts with the inventive CBPA (column A) and the prior art Methabenzthiazuron are summarized in Table I below. This table further includes compatibility data of three types of crop plants for the tested composition. Crop compatibility was rated according to the evaluation scale of the "European Weed Research Council (EWRC)." In this scale, numeral 1 indicates complete absence of plant damage symptoms while numeral 9 indicates complete damage. For practical purposes, the crop tolerance limit is assumed to be between numerals 4 and 5.

TABLE I

Herbicidal % effect on specific weeds versus amount of active ingredient applied:

| weed | amount a.i. applied per unit area | 2.65 kg/ha (A) | 2.65 kg/ha (B) | 4.3 kg/ha (A) | 4.3 kg/ha (B) | 6.7 kg/ha (A) | 6.7 kg/ha (B) |
|---|---|---|---|---|---|---|---|
| Shepherds Purse (*Capsella bursa-pastoris*) | | 84 | 95 | 96 | 99 | 100 | 100 |
| Lambs Quarters (*Chenopodium album*) | | 83 | 87 | 100 | 94 | 100 | 98 |
| Rough Henbit (*Lamium purpureum*) | | 89 | 0 | 91 | 73 | 97 | 80 |
| Camomile (*Matricaria chamomilla*) | | 70 | 88 | 90 | 100 | 100 | 100 |
| Chickweed (*Stellaria media*) | | 83 | 100 | 100 | 100 | 100 | 100 |
| Average weed effect (%) | | 81.8 | 74 | 95.4 | 91.5 | 99.4 | 95.6 |
| Crop compatibility (EWRC-evaluation): | | | | | | | |
| Green beans | | 1 | 1 | 1 | 1 | 1 | 1 |
| Barley | | 1 | 1 | 1 | 1 | 2 | 5 |
| Corn (*Zea mais*) | | 1 | 1 | 1 | 1 | 1 | 1 |

When the same procedure as set forth above is used to treat a weed infested crop area in the two to four leave state (both weeds and crops), positive results are obtained with the inventive composition indicating that CBPA or the salts thereof in addition to having a residual effectiveness have a remarkable contact effect as well.

Further tests made in the above manner showed a remarkable effectiveness of CBPA and its salts for control of weeds of the Graminae family, specifically Barnyard Grass (*Echinochloa crus-galli*), Annual meadow grass (*Poa annua*) and Common wild oat (*Avena fatua*).

EXAMPLE 8

Green-house tests were made to determine the activity of CBPA in the control of Wild oat (*Avena fatua*), a very noxious weed in many crop cultures. The test plants were seeded and cultured in pots at temperatures of 20° to 21° C. Effectivity tests were made when the plants had reached the two-leave to four-leave state, i.e. when the total plant height was about 10 to 12 cm. The amount of water applied in addition to the composition was equivalent to 1000 liters per hectare in each case. As a comparative substance (formulated in the same manner as the inventive CBPA or its salts) a recently developed standard herbicide, Diclofop-methyl, (BSI-approved common name) was used.

The effects were rated again by the EWRC-scale mentioned above and the results are given in Table II below indicating the results at varying amounts of the applied substance (in kilograms of active substance per hectare) after 7, 14 and 21 days subsequent to the treatment. Column A of Table II shows the results obtained with the inventive CBPA composition, while column C indicates the results obtained with the comparative compound.

TABLE II

| Evaluation after | Amount of active ingredient per unit area | | | | | | | |
|---|---|---|---|---|---|---|---|---|
| | 1 kg/ha | | 2 kg/ha | | 4 kg/ha | | 8 kg/ha | |
| | (A) | (C) | (A) | (C) | (A) | (C) | (A) | (C) |
| 7 days | 3 | 2 | 4 | 3 | 5 | 5 | 5 | 5 |
| 14 days | 4 | 4 | 6 | 5 | 9 | 7 | 9 | 6 |
| 21 days | 4 | 4 | 8 | 5 | 9 | 8 | 9 | 8 |

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A method for destroying dicotyledonous weeds in a crop area comprising treating said crop area with an effective amount of at least one active ingredient selected from the group consisting of 4-(4'-chlorobenzyl)-phenoxy acetic acid and the agriculturally acceptable salts of said acid with a base selected from the group consisting of inorganic and organic bases.

* * * * *